United States Patent [19]

McLane et al.

[11] 4,036,940
[45] July 19, 1977

[54] RECOVERY OF IODINE

[75] Inventors: Martin M. McLane, Texas City; Raymond A. Newsom, Dickinson, both of Tex.

[73] Assignee: Monsanto Company, St. Louis, Mo.

[21] Appl. No.: 644,497

[22] Filed: Dec. 29, 1975

[51] Int. Cl.$^2$ .............................................. C01B 7/14
[52] U.S. Cl. .................................. 423/503; 423/500; 55/71; 252/465
[58] Field of Search ................... 423/503, 500; 55/71; 252/465

[56] References Cited

U.S. PATENT DOCUMENTS

| 1,604,153 | 10/1926 | Ellinger | 423/503 X |
| 1,708,287 | 4/1929 | Turrentine | 423/503 |
| 3,493,325 | 2/1970 | Roth | 252/465 X |
| 3,658,467 | 4/1972 | Maeck | 55/71 X |
| 3,838,554 | 10/1974 | Wilhelm et al. | 55/71 |
| 3,880,619 | 4/1975 | Richardson et al. | 55/71 |

*Primary Examiner*—Edward Stern
*Attorney, Agent, or Firm*—Elizabeth F. Sporar

[57] ABSTRACT

Iodine is recovered from a process stream containing it or iodine-containing compounds by passing said stream while in the vapor state in contact with a solid treating agent or adsorbent comprising alumina impregnated with the oxides of copper and chromium and thereafter subjecting said solid treating agent to heating to a temperature from about 400° to about 600° C while passing a stream containing air or oxygen over it. The resulting effluent gas containing iodine can be fed directly back to the process from which it was derived or otherwise treated as by sublimation, for example, if desired.

5 Claims, No Drawings

RECOVERY OF IODINE

BACKGROUND OF THE INVENTION

The present invention relates to a process for the recovery of iodine employed in chemical processes. More particularly, it relates to iodine recovery for re-use in processes wherein iodine and/or iodine-containing compounds are employed, notably dehydrogenation processes.

Processes wherein certain hydrocarbons are converted to less saturated hydrocarbons by dehydrogenation in which iodine is employed are well known in the art. These dehydrogenation reactions include, for example, the conversion of paraffins to olefins and diolefins, of olefins to diolefins, of certain parrafins to aromatics (dehydrocyclization) and of alkyl aromatics to vinyl aromatics including hydrocoupling as in the conversion of toluene to stilbene. Such iodinative dehydrogenation processes employ iodine as such or iodine in conjunction with oxygen whereby the hydrogen iodide simultaneously formed in the reactions is converted under the reaction conditions to elemental iodine. In some processes, there is also a concomitant production of organic and inorganic iodides as by-products. In order for such processes to be economically feasible, iodine utilization must be maintained at a high level which requires efficient recovery of the iodine from process streams containing it for re-use in the process. Also, the removal of iodine from reaction effluents has a salutary effect in some instances. In the production of stilbene, for example, by dehydrocoupling of toluene in the presence of iodine, the removal of inorganic iodine from the reaction effluent facilitates purification of the stilbene by distillation to a product having > 99% purity which is essentially free of iodine. It is, accordingly, an object of the present invention to provide a process which provides for recovery of iodine from process streams at a high level of efficiency. Other objects and advantages of the invention will become apparent from the following description thereof.

SUMMARY OF THE INVENTION

According to the present invention, a process stream such as the reaction product or effluent from a reaction wherein iodine is employed as a reactant or catalyst and which contains iodine or iodine-containing compounds is passed while in the vapor state in contact with a solid treating agent or adsorbent comprising alumina impregnated with the oxides of copper and chromium. The solid treating agent is then subjected to heating at a temperature from about 400° to about 600° C while passing a stream of oxygen, air, inert gas and air, or inert gas and oxygen over it and the resulting effluent gas containing iodine can be fed directly back to the process from which it was derived for utilization as a reactant or otherwise treated as by sublimation, for example, for recovery of the iodine if this is desirable. The treated process stream free of said iodine or iodine-containing componds may then be utilized as such or subjected to the usual treatments for separation of the desired products therefrom such as, for example, by quenching of said effluent either with organic compounds or with water to remove all condensibles from the stream and separation of these by distillation and/or other well known techniques with the non-condensible gases being passed through suitable scrubbing liquids for removal of any residual compounds of value in the system.

DESCRIPTION OF THE PREFERRED EMBODIMENTS

The invention will be best understood from a consideration of the following examples. The process of the invention is generally applicable to the recovery of iodine or iodine-containing compounds from any process stream containing these as components. However, for purposes of illustration, the examples given are directed to the treatment of the reaction effluent obtained in the production of stilbene from toluene by dehydrocoupling but these are not to be considered as unduly limiting the invention in any manner whatsoever.

EXAMPLE 1

The reactor employed for the conversion of toluene to stilbene was of the fluidized-bed type consisting of quartz tubing 50 mm in inside diameter, approximately 92 cm in overall length, terminating at its lower end in a 60°-cone and having an upper disengaging section of 90 mm inside diameter about 15 mm long. A ¼-inch Type 316 stainless steel thermowell was located in the center of the reactor which was packed with about 1600g of a 150-$\mu$ commercial alpha-alumina known to the trade as "Alundum." Temperature was controlled by external electric heaters and variacs.

The iodine recovery unit installed downstream of the reactor was a 30-mm I.D. tubular quartz vessel 54 cm long of similar shape to the reactor equipped with a 6-mm I.D. Vycor thermowell entering the top and extending the length thereof in which thermocouples connected to a temperature recorder were installed. Temperatures were controlled manually by external electric heaters connected to variacs. The unit was packed with a solid treating agent or adsorbent consisting of copper oxide (4.72 wt% as Cu) and chromium oxide (0.94 wt% as Cr) impregnated on 20-mesh commercial alpha-alumina. The commercial alpha-alumina used was "Alundum" having a typical chemical analysis as follows: $Al_2O_3$—84.7%; $SiO_2$—13.4%; $Fe_2O_3$—0.20%; $TiO_2$—0.30%; CaO—0.2%; MgO—0.04%; $Na_2O$—0.60%; $K_2O$—0.70%; a bulk density of 1.4 to 1.6 g/cc, an apparent specific gravity of 3.3 to 3.6, a packing density of 44–48 lb/cu ft., and a surface area from 0.5–1m²/g. The treating agent was prepared by dissolving copper and chromium nitrates in water and contacting sufficient quantities of these solutions with the solid support to achieve the desired amount of impregnation when the material was dried. The resulting slurry was placed in a rotating evaporator and dried using both heat and vacuum and then calcined to drive off $NO_2$. Prior to use the impregnated material was treated by passing a stream of hydrogen through it while it was maintained at a temperature of from 400° to 450° C until the copper on the treating agent turned a characteristic red color indicating reduction had taken place.

Before introduction into the bottom of the reactor, the reactants were vaporized and preheated. Fluidization of the bed was effected by means of nitrogen while the desired temperature in the bed was established (550°– 580° C). A mixture of toluene, radioactively-tagged elemental iodine, and oxygen (air) in a molar ratio of 1.0/0.005/0.38 was continuously introduced into the reactor maintained at about 575° C and at a pressure slightly above atmospheric. A minor portion of the effluent from the top of the reactor was continuously withdrawn, separated and analyzed by gas chromatography. The remaining major portion of the effluent was continuously passed through the iodine recovery unit maintained at a temperature from about 350° to about 400° C and at a rate of 4.3g/min. The effluent from the recovery unit was partially condensed to remove stilbene therefrom followed by further condensation to recover the remainder of the condensibles with the condensates being recovered in two different separators. Various scrubbers and traps were used to capture any iodine or organic materials leaving the separation system. After a three-hour run, the unit was disassembled, product and unreacted material removed, and the various pieces of equipment washed with ethylbenzene. The quantity of iodine present in each sample was determined by radioactive tracer analysis. Also, the catalyst was removed from the reactor and the iodine present determined by tracer analysis. The iodine recovery unit was removed intact and the iodine present therein also determined. All samples which could be analyzed chemically for iodine were so analyzed. The catalyst was replaced in the reactor and the iodine present was removed by passing heated air through the fluidized bed. The iodine in the effluent gas was absorbed in scrubbers with the scrubber samples being analyzed for iodine by both chemical and radioactive methods. The iodine recovery unit was reassembled and regenerated by passing air through it while it was maintained at a temperature of 550° C. The effluent gases were scrubbed with potassium iodate, carbon tetrachloride and water to remove iodine. The scrubber samples and related equipment were all analyzed for iodine. Results of all analyses are presented in Table 1. These data show that during the run the major portion of the iodine fed, 88.52%, was retained in the iodine recovery unit and of the iodine flowing to the recovery unit, 93.7% was retained therein (88.52/94.44). No inorganic iodine was present downstream in the separator samples. The regeneration to remove iodine from the iodine recovery unit resulted in removal of all but 1% of the iodine adsorbed therein.

EXAMPLE 2

A three-hour run was made essentially like that in Example 1 except that the treating material in the iodine recovery unit was not subjected to reduction treatment with hydrogen prior to the run. The reaction effluent stream was depended on for reduction of the copper and chromium oxides. Results are presented in Table 2. Again, it will be seen that the iodine recovery unit removes the major part of the iodine from the reaction effluent stream (75.62%) and about 85.9% of the iodine flowing to the recovery unit. Also, no inorganic iodine was present downstream of the recovery unit in this run.

As indicated previously, the iodine recovery process of the invention is applicable to any process stream containing iodine or iodine compounds. The iodine recovery process is applicable in particular to process streams produced in iodinative dehydrogenations of organic compounds and especially of hydrocarbons. Comprehensive lists of such compounds which can be so dehydrogenated are to be found in a number of patents, for example, a representative list is disclosed in U.S. Pat. No. 3,310,590 Column 3, lines 23–50.

TABLE 1

| | Iodine, Percent of That Fed | |
|---|---|---|
| | DETECTED BY | |
| ITEM | Chemical Analysis | Radioactive Tracer |
| Reaction | | |
| Feed Line | 0.10 | 0.10 |
| Spillage | — | 0.27 |
| Toluene Vaporizer | — | 0.49 |
| Catalyst | — | 0.39 |
| Separator-3 | | |
| EB Wash | 2.13 | 2.28 |
| Water Wash | 0.00 | 0.69 |
| Transfer Line | — | 0.48 |
| Iodine Recovery Unit | — | 88.52 |
| Partial Condenser | — | 0.01 |
| Separator-1 Solids | 1.32 | 1.26 |
| Separator-2 | 0.00 | 0.00 |
| Separator-2 | 1.18 | 1.22 |
| Separator-2 | 3.11 | 3.14 |
| Separator-2 FB Wash | 0.20 | 0.19 |
| EB Scrubber No. 1 | 0.97 | 0.10 |
| EB Scruber No. 2 | 0 | 0.00 |
| | | 99.14 |
| REGENERATION | | |
| Reactor | | |
| Scrubber No. 1 | 0.83 | 0.86 |
| Scrubber No. 2 | 0.03 | 0.01 |
| Iodine Recovery Unit | | |
| Scrubber No. 1-1 | 72.09 | 71.97 |
| Scrubber No. 2-1 | 0.42 | 0.45 |
| Scrubber No. 1-2 | 1.58 | 1.67 |
| Scrubber No. 2-2 | 0.28 | 0.02 |
| Scrubber No. 3 | — | 0.11 |
| Scrubber No. 4 | 0.27 | 0.32 |
| Scrubber No. 5 | 0.04 | 0.05 |
| Scrubber Assembly | — | 1.83 |
| Plastic Tubing | — | 6.54 |
| Iodine Recovery Unit Assembly | — | 1.07 |
| | | 84.04 |

TABLE 2

| | Iodine, Percent of That Fed | |
|---|---|---|
| | DETECTED BY | |
| ITEM | Chemical Analysis | Radioactive Tracer |
| Reaction | | |
| Feed Line | 0.15 | 0.19 |
| Spillage | — | 0.06 |
| Toluene Vaporizer | — | 0.83 |
| Catalyst | — | 0.38 |
| Separator-3 | | |
| EB Wash | 0.24 | 0.19 |
| Water Wash | 0.05 | 0.04 |
| Transfer Line | — | 1.11 |
| Iodine Recovery Unit | — | 75.62 |
| Partial Condenser | 0.13 | — |
| Separator-1 Solids | 2.76 | 2.28 |
| Separator-1 EB Wash | 0.06 | 0.01 |
| Separator-2 | 11.18 | 9.57 |
| Separator-2 | — | 0.02 |
| Separator-2 EB Wash | — | 0.43 |
| EB Scrubber No. 1 | 0.15 | 0.05 |
| EB Scrubber No. 2 | 0.12 | 0.03 |
| Scrubber No. 3($KIO_3$) | — | 0.02 |
| Scrubber No. 4($CCl_4$) | 0.00 | 0.01 |
| Scrubber No. 5($H_2O$) | 0.00 | 0.01 |
| | | 90.85 |
| REGENERATION | | |
| Reactor | | |
| Scrubber No. 1 | 0.19 | |
| Scrubber No. 2 | 0.08 | 0.27 |
| Iodine Recovery Unit | | |
| Scrubber No. 1-1 | 62.92 | |
| Scrubber No. 2-1 | 0.13 | |
| Scrubber No. 1-2 | 3.65 | |
| Scrubber No. 2-2 | | |
| Scrubber No. 3 | 0.00 | |
| Scrubber No. 4 | 0.00 | |
| Scrubber No. 5 | 0.00 | 66.70 |

Since the dehydrogenation step proper constitutes no part of the present invention, it is superfluous to discuss any details thereof such as suitable catalysts, temperatures, pressures, reactant ratios, etc.

The solid treating agent employed for iodine recovery herein comprises alumina impregnated with the oxides of copper and chromium. The quantity of these metal oxides coated on the alumina can vary. Generally an amount of copper oxide from about 5 to about 25 percent by weight as Cu and from about 1 to about 5% by weight of chromium oxide as Cr will be used. Preferred treating agents or adsorbents will contain from about 5% to about 10% by weight of copper oxide as Cu and from about 1% to about 2% by weight of chromium oxide as Cr.

Preferably, the alumina employed is of the alpha type although other forms of alumina are suitable. The surface area of the alumina is not critical and may range between $0.5 m^2/g$ to $40 m^2/g$ although alumina having a surface area from about 0.5 to about $10 m^2/g$ is preferred. The oxides may be deposited upon the alumina in any suitable manner. Preferably, the alumina is slurried with an aqueous solution of the soluble salts of Cu and of Cr such as, for example, the sulfates, nitrates, and the like, the slurry is dried and calcined at temperatures from about 500° to about 700° C for from about 1 to about 12 hours to convert the metal compounds to the oxide. The calcined material may be tableted or pelletized for use in fixed bed reactors or may be pulverized and sized for use in fluidized bed reactors. In the preferred mode of operation, the solid treating agent or adsorbent is treated with hydrogen, carbon monoxide or other reducing agent to reduce the metal oxides present to their elemental form prior to use but this step is not necessary when the process streams to be treated contain either or both of these or other reducing agents.

Contacting of the process stream and the solid treating agent can be effected with the stream in the vapor phase and the adsorbent in either a fixed, moving or fluidized bed but a fixed bed operation is preferred. Contacting is effected at various temperatures depending upon the constitution of the iodine-containing stream. The contact temperature should be maintained sufficiently high to prevent condensation or crystallization of any of the components of the stream being contacted with the treating agent. Generally, a temperature within the range from about 300° to about 500° C is satisfactory while preferred temperatures are in the range from about 400° to about 450° C.

The iodine removed is regenerated by heating the exhausted treating agent to a temperature from about 400° to about 650° C and preferably from about 500° to about 550° C while passing oxygen, air or a combination of oxygen or air and nitrogen through the bed. The length of time required for regeneration of the treating agent depends on the size of the bed and the degree of depletion of its activity. In general, the regeneration period may range from 1 to about 12 hours but usually periods from about 4 to about 8 hours will be satisfactory. The iodine evolved can either be used in the vapor state as such, absorbed in a solvent or sublimed for storage as a solid material as desired. In actual practice, the iodine recovery step would be effected as a cyclic operation. As the capacity to remove iodine is approached in one bed, the process stream being treated would be switched to a fresh bed and the exhausted one regenerated. The exit gas from the iodine recovery unit can then be cooled and fed to a scrubber having the dehydrogenatable hydrocarbon, such as toluene, for example, as the absorbing liquid. The hydrocarbon and iodine from the scrubber bottoms would be recycled to the reactor. Following regeneration, reducing gas, which could be off-gas from the reactor, would be passed through the bed.

What is claimed is:

1. A process for recovery of iodine from a process stream containing iodine or iodine-containing reaction products and a reducing agent which comprises passing said stream while in the vapor state in contact with a treating agent comprising alumina impregnated with the oxides of copper and chromium wherein the amount of copper oxide is from about 5 to about 25 wt.% as Cu and the amount of chromium oxide is from about 1 to about 5 wt.% as chromium, said contacting being effected at a temperature from about 300° to about 500° C, and thereafter regenerating said treating agent by heating it while passing oxygen, air, oxygen — inert gas or air — inert gas mixtures therethrough at a temperature from about 400° to about 600° C for a period from about 1 to about 12 hours.

2. The process of claim 1 wherein said alumina is alpha-alumina.

3. The process of claim 2 wherein the amount of copper oxide is from about 5% to about 10% by weight as Cu and the amount of chromium oxide is from about 1 to about 2% by weight as Cr.

4. The process of claim 3 wherein said regeneration is effected by heating over a period of from about 4 about 8 hours.

5. A process for recovery of iodine from a process stream containing iodine or iodine-containing reaction products which comprises passing said stream while in the vapor state at a temperature from about 300° to about 500° C in contact with a treating agent comprising alumina impregnated with the oxides of copper and chromium wherein the amount of copper oxide is from about 5 to about 25 wt.% as Cu and the amount of chromium oxide is from about 1 to about 2 wt.% as chromium, said treating agent having been subjected prior to use to treatment with a reducing agent to reduce the metal oxides present to their elemental forms, and thereafter regenerating said treating agent by heating it while passing oxygen, air, oxygen — inert gas or air — inert gas mixtures therethrough at a temperature from about 400° to about 600° C for a period from about 1 to about 12 hours.

* * * * *